(12) United States Patent
Trauner et al.

(10) Patent No.: US 8,951,995 B2
(45) Date of Patent: Feb. 10, 2015

(54) USE OF 24-NOR-UDCA

(75) Inventors: Michael Trauner, Graz (AT); Alan Hofmann, La Jolla, CA (US); Peter Fickert, Graz (AT)

(73) Assignee: Medizinische Universitat Graz, Graz (AT)

( * ) Notice: Subject to any disclaimer, the term of this patent is extended or adjusted under 35 U.S.C. 154(b) by 1919 days.

(21) Appl. No.: 11/914,211

(22) PCT Filed: May 12, 2005

(86) PCT No.: PCT/EP2005/052178
§ 371 (c)(1),
(2), (4) Date: Nov. 20, 2008

(87) PCT Pub. No.: WO2006/119803
PCT Pub. Date: Nov. 16, 2006

(65) Prior Publication Data
US 2009/0163459 A1  Jun. 25, 2009

(51) Int. Cl.
A61K 31/575 (2006.01)
(52) U.S. Cl.
CPC .................................. A61K 31/575 (2013.01)
USPC ........................................................ 514/182
(58) Field of Classification Search
CPC .................................................... A61K 31/575
USPC ........................................................ 514/182
See application file for complete search history.

(56) References Cited

U.S. PATENT DOCUMENTS 4,892,868 A    1/1990  Castagnola et al. .......... 514/182

FOREIGN PATENT DOCUMENTS

| EP | 0 393 494 | 10/1990 |
| EP | 0 624 595 | 11/1994 |
| EP | 0 652 773 | 5/1995 |
| EP | 1 317 925 | 6/2003 |

OTHER PUBLICATIONS

Mayo Clinic: Cystic Fibrosis (Jun. 13, 2012). Accessed at http://www.mayoclinic.org/diseases-conditions/cystic-fibrosis/basics/complications/con-20013731 on May 28, 2014.*
"Data Sheet URSOFALK," http://www.medsafe.govt.nz/profs/datasheet/u/ursofalkcap.htm, retrieved Dec. 16, 2005, last updated 2004.
Bolder et al., "Sulindac is excreted into bile by a canalicular bile salt pump and undergoes a cholehepatic circulation in rats," *Gastroenterology*, 117:962-971, 1999.
Broderick et al., "Correcting biliary phenotype in cystic fibrosis (CF) mice: Nor-ursodeoxycholic acid (nor-UDCA), but not UDCA, normalizes hepatic bile pH and increases bile flow in G551D CF mice," *Hepatology*, 36(4 Pt.2):337A, 2002.

Cohen et al., "Differing effects of nor-ursodeoxycholic or ursodeoxycholic acid on hepatic histology and bile acid metabolism in the rabbit," *Gastroenterology*, 91:189-197, 1986.
Fickert et al., "Effects of ursodeoxycholic and cholic acid feeding on hepatocellular transporter expression in mouse liver," *Gastroenterology*, 121:170-183, 2001.
Fickert et al., "Regurgitation of bile acids from leaky bile ducts causes sclerosing cholangitis in Mdr2 (Abcb4) knockout mice," *Gastroenterology*, 127:261-274, 2004.
Fickert et al., "Ursodeoxycholic acid aggravates bile infarcts in bile duct-ligated and Mdr2 knockout mice via disruption of cholangioles," *Gastroenterology*, 123:1238-1251, 2002.
Ismail et al., "Treatment of progressive familial intrahepatic cholestasis: liver transplantation or partial external biliary diversion," *Pediatr. Transplant.*, 3:219-224, 1999.
Jacquemin et al., "Ursodeoxycholic acid therapy in pediatric patients with progressive familial intrahepatic cholestasis," *Hepatology*, 25:519-523, 1997.
Jacquemin, "Progressive familial intrahepatic cholestasis. Genetic basis and treatment," *Clin. Liver Dis.*, 4:753-763, 2000.
Jansen and Sturm, "Genetic cholestasis, causes and consequences for hepatobiliary transport," *Liver Int.*, 23:315-322, 2003.
Johnson et al., "Radioassay of bile acid coenzyme A:glycine/taurine: N-acyltransferase using an n-butanol solvent extraction procedure," *Anal. Biochem.*, 182:360-365, 1989.
Lammert et al., "Spontaneous cholecysto- and hepatolithiasis in Mdr2-/- mice: a model for low phospholipid-associated cholelithiasis," *Hepatology*, 39:117-128, 2004.
Paumgartner and Beuers, "Ursodeoxycholic acid in cholestatic liver disease: mechanisms of action and therapeutic use revisited," *Hepatologyy*, 36:525-531, 2002.
Pikarsky et al., "NF-kappaB functions as a tumour promoter in inflammation-associated cancer," *Nature*, 431:461-466, 2004.
Schmassmann et al., "Prevention of ursodeoxycholate hepatotoxicity in the rabbit by conjugation with N-methyl amino acids," *Hepatology*, 11:989-996, 1990.
Schteingart and Hofmann, "Synthesis of 24-nor-5 beta-cholan-23-oic acid derivatives: a convenient and efficient one-carbon degradation of the side chain of natural bile acids.," *J. Lip. Res.*, 29:1387-1395, 1988.
Trauner and Graziadei, "Review article: mechanisms of action and therapeutic applications of ursodeoxycholic acid in chronic liver diseases," *Aliment Pharmacol. Ther.*, 13:979-996, 1999.
Wagner et al., "Role of farnesoid X receptor in determining hepatic ABC transporter expression and liver injury in bile duct-ligated mice," *Gastroenterology*, 125:825-838, 2003.
Whitington et al., "Cholestasis," http://www.emedicine.com/ped/topic383.htm, retrieved Dec. 16, 2005, last updated 2004.
Yoon et al., "Effect of side-chain shortening on the physiologic properties of bile acids: hepatic transport and effect on biliary secretion of 23-nor-ursodeoxycholate in rodents," *Gastroenterology*, 90:837-852, 1986.

(Continued)

*Primary Examiner* — Barbara P Badio
*Assistant Examiner* — Sara E Townsley
(74) *Attorney, Agent, or Firm* — Fulbright & Jaworski LLP

(57) ABSTRACT

The present invention relates to the use of nor-ursodeoxycholic acid for the manufacture of a drug for the treatment and/or the prevention of liver diseases, preferably chronic liver diseases.

5 Claims, 5 Drawing Sheets

(56) References Cited

OTHER PUBLICATIONS

Figure 1:
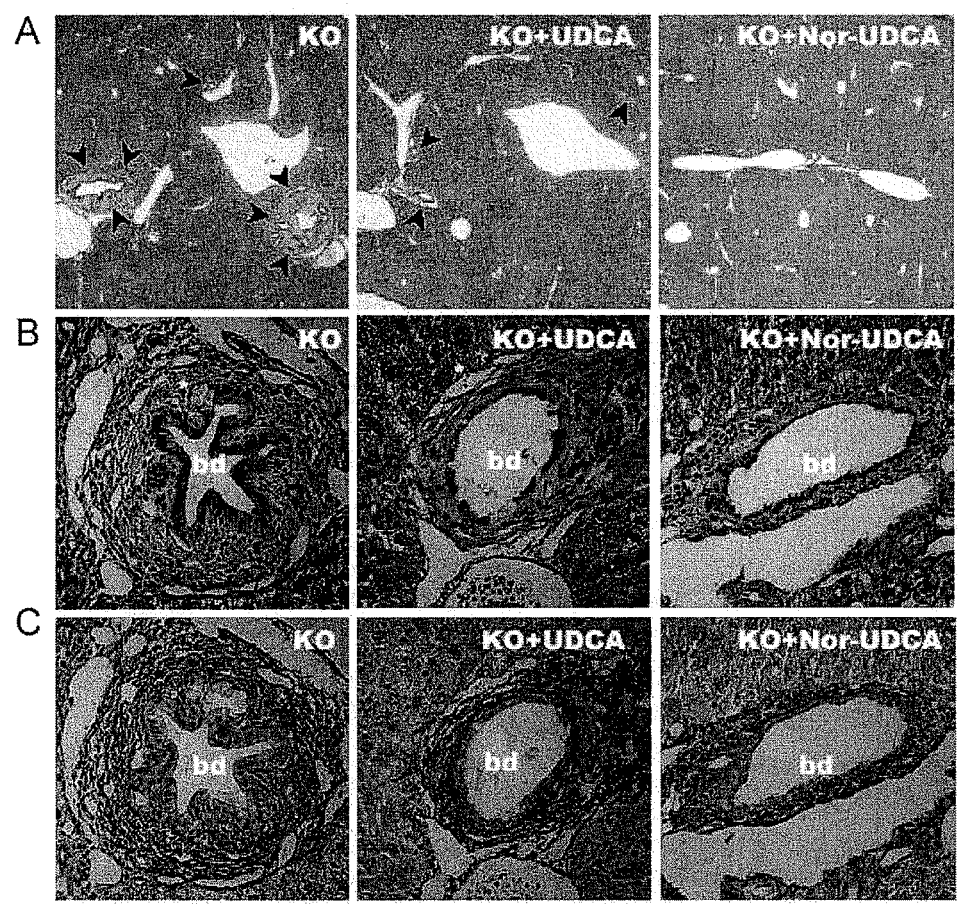

Beraza et al., "Nor-ursodeoxycholic acid reverses hepatocyte-specific nemo-dependent steatohepatitis," *Gut*, 60:387-396, 2011.

Czaja and Carpenter, "Decreased fibrosis during corticosteroid therapy of autoimmune hepatitis," *J. Hepatology*, 40:646-552, 2004.

Engstrom et al., "Primary neoplasms of the liver," Ed. Bast et al., *Holland-Frei Cancer Medicine*, 5th Edition, 1392-1401, 2000.

European Search Report issued in European Patent Application No. 11176270, dated Nov. 25, 2011.

European Search Report issued in European Patent Application No. 11176271, dated Nov. 30, 2011.

European Search Report issued in European Patent Application No. 11176272 dated Dec. 2, 2011.

Feher and Lengyel, "A new approach to drug therapy in non-alcoholic steatohepatitis (NASH)," *The Journal of International Medical Research*, 31:537-551, 2003.

Halilbasic et al., "Side chain structure determines unique physiologic and therapeutic properties of *nor*Usodeoxycholic acid in Mdr2-/- mice," *Hepatology*, 49(6): 1972-1981, 2009.

Junge et al., "Withdrawal of steroids: A randomized prospective study of prednisone and tacrolimus versus mycophenolate mofetil and tacrolimus in liver transplant recipients with autoimmune hepatitis," *Transplantation Proceedings*, 37: 1695-1696, 2005.

Krawitt, "Autoimmune hepatitis: classification, heterogeneity, and treatment," *American Journal of Medicine*, 96(suppl 1A): 23S-26S, 1994.

Lindor et al., "Ursodeoxycholic acid for treatment of nonalcoholic steatohepatitis: results of a randomized trial," *Hepatology*, 39(3): 770-778, 2004.

Nakamura et al., "Efficacy of ursodeoxycholic acid in Japanese patients with type 1 autoimmune hepatitis," *J. Gastroenterology and Hepatology*, 13:490-495, 1998.

Ponsioen, "Novel developments in IBD-related sclerosing cholangitis," *Best Practice & Research Clinical Gastroenterology*, 25(Supl 1): S15-S18, 2011.

Triger, "Autoimmune chronic active hepatitis and primary biliary cirrhosis," *Baillieres Clinical Gastroenterology*, 3(1): 21-38, 1989.

Tsagarakis et al., "A concentration-dependent effect of ursodeoxycholate on apoptosis and caspases activities of HepG2 hepatocellular carcinoma cells," *European Journal of Pharmacology*, 640:1-7, 2010.

Zen et al., "Are bile duct lesions of primary biliary cirrhosis distinguishable from those of autoimmune hepatitis and chronic viral hepatitis? Interobserver histological agreement on trimmed bile ducts," *J. Gastroenterol.*, 40:164-170, 2005.

Lindor et al., "High dose ursodeoxycholic acid for the treatment of primary sclerosing cholangitis," author manuscript, NIH Public Access, PMCID: PMC2758780, available in PMC Oct. 7, 2009.

Velayudham and Farrell, "Drug-induced cholestasis," *Expert Opin. Drug Saf.*, 2(3):287-304, 2003.

Sundaram and Sokol, "The multiple facets of ABCB4 (MDR3) deficiency," *Current Treatment Options in Gastroenterology*, Current Medicine Group LLC, 10:495-503, 2007.

\* cited by examiner

Fig. 5
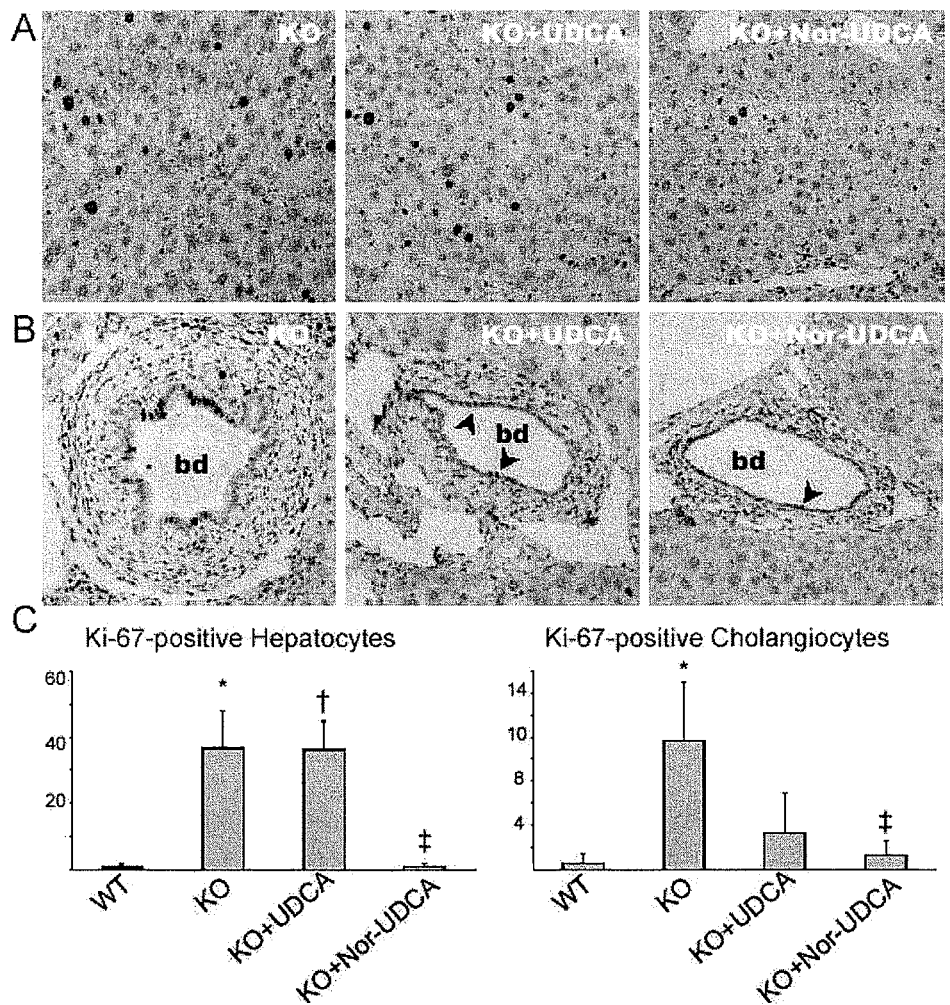
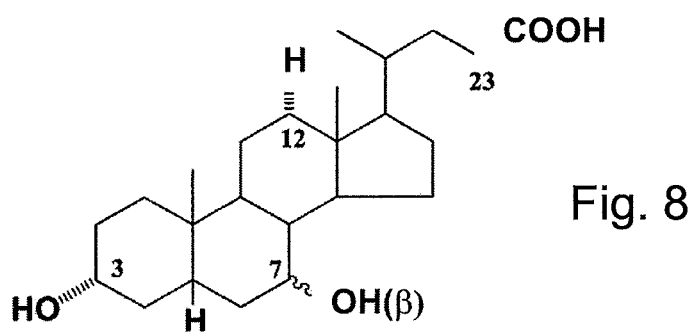
Fig. 8

SEQUENCE LISTING

<160> NUMBER OF SEQ ID NOS: 43

<210> SEQ ID NO 1
<211> LENGTH: 19
<212> TYPE: DNA
<213> ORGANISM: Artificial
<220> FEATURE:
<223> OTHER INFORMATION: Synthetic primer

<400> SEQUENCE: 1
caatgggaac gttggaaga                                                    19

<210> SEQ ID NO 2
<211> LENGTH: 20
<212> TYPE: DNA
<213> ORGANISM: Artificial
<220> FEATURE:
<223> OTHER INFORMATION: Synthetic primer

<400> SEQUENCE: 2
tgatgcactg gaagaggaac                                                   20

<210> SEQ ID NO 3
<211> LENGTH: 20
<212> TYPE: DNA
<213> ORGANISM: Artificial
<220> FEATURE:
<223> OTHER INFORMATION: Synthetic primer

<400> SEQUENCE: 3
ccaccagtag cacactttcc                                                   20

<210> SEQ ID NO 4
<211> LENGTH: 22
<212> TYPE: DNA
<213> ORGANISM: Artificial
<220> FEATURE:
<223> OTHER INFORMATION: Synthetic primer

<400> SEQUENCE: 4
ttccatctcc atcacagtat ca                                                22

<210> SEQ ID NO 5
<211> LENGTH: 22
<212> TYPE: DNA
<213> ORGANISM: Artificial
<220> FEATURE:
<223> OTHER INFORMATION: Synthetic primer

<400> SEQUENCE: 5
ctggtgtgtg acgttcccat ta                                                22

<210> SEQ ID NO 6
<211> LENGTH: 18
<212> TYPE: DNA
<213> ORGANISM: Artificial
<220> FEATURE:
<223> OTHER INFORMATION: Synthetic primer

<400> SEQUENCE: 6
ccgacagcac gaggctttt                                                    18

<210> SEQ ID NO 7
<211> LENGTH: 18
<212> TYPE: DNA
<213> ORGANISM: Artificial
<220> FEATURE:
<223> OTHER INFORMATION: Synthetic primer

<400> SEQUENCE: 7
gccaggaccg ctcagaga                                                     18

<210> SEQ ID NO 8

```
<211> LENGTH: 22
<212> TYPE: DNA
<213> ORGANISM: Artificial
<220> FEATURE:
<223> OTHER INFORMATION: Synthetic primer

<400> SEQUENCE: 8
tgcctcgact gttagtcaag ca                                          22

<210> SEQ ID NO 9
<211> LENGTH: 21
<212> TYPE: DNA
<213> ORGANISM: Artificial
<220> FEATURE:
<223> OTHER INFORMATION: Synthetic primer

<400> SEQUENCE: 9
gcccaccaag aacgatagtc a                                           21

<210> SEQ ID NO 10
<211> LENGTH: 22
<212> TYPE: DNA
<213> ORGANISM: Artificial
<220> FEATURE:
<223> OTHER INFORMATION: Synthetic primer

<400> SEQUENCE: 10
gaaggcaact ggatggaagt ct                                          22

<210> SEQ ID NO 11
<211> LENGTH: 24
<212> TYPE: DNA
<213> ORGANISM: Artificial
<220> FEATURE:
<223> OTHER INFORMATION: Synthetic primer

<400> SEQUENCE: 11
cccaccaagt ctaactctct ggaa                                        24

<210> SEQ ID NO 12
<211> LENGTH: 21
<212> TYPE: DNA
<213> ORGANISM: Artificial
<220> FEATURE:
<223> OTHER INFORMATION: Synthetic primer

<400> SEQUENCE: 12
gggtgctgac tgcatcaaag a                                           21

<210> SEQ ID NO 13
<211> LENGTH: 22
<212> TYPE: DNA
<213> ORGANISM: Artificial
<220> FEATURE:
<223> OTHER INFORMATION: Synthetic primer

<400> SEQUENCE: 13
cctcaacgga agaaccaaag ag                                          22

<210> SEQ ID NO 14
<211> LENGTH: 20
<212> TYPE: DNA
<213> ORGANISM: Artificial
<220> FEATURE:
<223> OTHER INFORMATION: Synthetic primer

<400> SEQUENCE: 14
```
ctcagacagc gaggcacatc                                          20

<210> SEQ ID NO 15
<211> LENGTH: 18
<212> TYPE: DNA
<213> ORGANISM: Artificial
<220> FEATURE:
<223> OTHER INFORMATION: Synthetic primer

<400> SEQUENCE: 15
ggcagggcca cactgagt                                            18

<210> SEQ ID NO 16
<211> LENGTH: 24
<212> TYPE: DNA
<213> ORGANISM: Artificial
<220> FEATURE:
<223> OTHER INFORMATION: Synthetic primer

<400> SEQUENCE: 16
agtcctcaga tgtcagccta gtga                                     24

<210> SEQ ID NO 17
<211> LENGTH: 20
<212> TYPE: DNA
<213> ORGANISM: Artificial
<220> FEATURE:
<223> OTHER INFORMATION: Synthetic primer

<400> SEQUENCE: 17
ttagatgggc ctctggttct                                          20

<210> SEQ ID NO 18
<211> LENGTH: 24
<212> TYPE: DNA
<213> ORGANISM: Artificial
<220> FEATURE:
<223> OTHER INFORMATION: Synthetic primer

<400> SEQUENCE: 18
gcccacaatt ccaattccaa cctt                                     24

<210> SEQ ID NO 19
<211> LENGTH: 20
<212> TYPE: DNA
<213> ORGANISM: Artificial
<220> FEATURE:
<223> OTHER INFORMATION: Synthetic primer

<400> SEQUENCE: 19
acatcaggtc ggccatcact                                          20

<210> SEQ ID NO 20
<211> LENGTH: 22
<212> TYPE: DNA
<213> ORGANISM: Artificial
<220> FEATURE:
<223> OTHER INFORMATION: Synthetic primer

<400> SEQUENCE: 20
cgtaccggat gagctgtgaa tt                                       22

<210> SEQ ID NO 21
<211> LENGTH: 20
<212> TYPE: DNA

<210> SEQ ID NO 21
<211> LENGTH: 20
<212> TYPE: DNA
<213> ORGANISM: Artificial
<220> FEATURE:
<223> OTHER INFORMATION: Synthetic primer

<400> SEQUENCE: 21
gcagggttcc aacgatgttg                                                  20

<210> SEQ ID NO 22
<211> LENGTH: 21
<212> TYPE: DNA
<213> ORGANISM: Artificial
<220> FEATURE:
<223> OTHER INFORMATION: Synthetic primer

<400> SEQUENCE: 22
gcagccatcg actaggacag a                                                21

<210> SEQ ID NO 23
<211> LENGTH: 23
<212> TYPE: DNA
<213> ORGANISM: Artificial
<220> FEATURE:
<223> OTHER INFORMATION: Synthetic primer

<400> SEQUENCE: 23
ggtggttttc agttcagcta tgg                                              23

<210> SEQ ID NO 24
<211> LENGTH: 23
<212> TYPE: DNA
<213> ORGANISM: Artificial
<220> FEATURE:
<223> OTHER INFORMATION: Synthetic primer

<400> SEQUENCE: 24
ctggaaagaa gtctgaggaa tgc                                              23

<210> SEQ ID NO 25
<211> LENGTH: 20
<212> TYPE: DNA
<213> ORGANISM: Artificial
<220> FEATURE:
<223> OTHER INFORMATION: Synthetic primer

<400> SEQUENCE: 25
tcgacatgga gctggtgaaa                                                  20

<210> SEQ ID NO 26
<211> LENGTH: 20
<212> TYPE: DNA
<213> ORGANISM: Artificial
<220> FEATURE:
<223> OTHER INFORMATION: Synthetic primer

<400> SEQUENCE: 26
ctggcgagcc ttagtttgga                                                  20

<210> SEQ ID NO 27
<211> LENGTH: 25
<212> TYPE: DNA
<213> ORGANISM: Artificial
<220> FEATURE:
<223> OTHER INFORMATION: Synthetic primer

<400> SEQUENCE: 27
gaccctcaca ctcagatcat cttct                                            25

<210> SEQ ID NO 28
<211> LENGTH: 20
<212> TYPE: DNA
<213> ORGANISM: Artificial
<220> FEATURE:
<223> OTHER INFORMATION: Synthetic primer

<400> SEQUENCE: 28
cctccacttg gtggtttgct                                           20

<210> SEQ ID NO 29
<211> LENGTH: 22
<212> TYPE: DNA
<213> ORGANISM: Artificial
<220> FEATURE:
<223> OTHER INFORMATION: Synthetic primer

<400> SEQUENCE: 29
tgcactaaac agcagaaccg ag                                        22

<210> SEQ ID NO 30
<211> LENGTH: 20
<212> TYPE: DNA
<213> ORGANISM: Artificial
<220> FEATURE:
<223> OTHER INFORMATION: Synthetic primer

<400> SEQUENCE: 30
ttgctcagcc tcatgcactg                                           20

<210> SEQ ID NO 31
<211> LENGTH: 21
<212> TYPE: DNA
<213> ORGANISM: Artificial
<220> FEATURE:
<223> OTHER INFORMATION: Synthetic primer

<400> SEQUENCE: 31
ggaaggacca cgactcataa c                                         21

<210> SEQ ID NO 32
<211> LENGTH: 25
<212> TYPE: DNA
<213> ORGANISM: Artificial
<220> FEATURE:
<223> OTHER INFORMATION: Synthetic primer

<400> SEQUENCE: 32
gattcttcac aaggtttgtg ttacc                                     25

<210> SEQ ID NO 33
<211> LENGTH: 21
<212> TYPE: DNA
<213> ORGANISM: Artificial
<220> FEATURE:
<223> OTHER INFORMATION: Synthetic primer

<400> SEQUENCE: 33
tctgagccct gcatctatct g                                         21

<210> SEQ ID NO 34
<211> LENGTH: 19
<212> TYPE: DNA
<213> ORGANISM: Artificial
<220> FEATURE:

<223> OTHER INFORMATION: Synthetic primer

<400> SEQUENCE: 34
ccccagaggc gttgacata                                              19

<210> SEQ ID NO 35
<211> LENGTH: 24
<212> TYPE: DNA
<213> ORGANISM: Artificial
<220> FEATURE:
<223> OTHER INFORMATION: Synthetic primer

<400> SEQUENCE: 35
caatgcaatg aagaactgga ctgt                                        24

<210> SEQ ID NO 36
<211> LENGTH: 24
<212> TYPE: DNA
<213> ORGANISM: Artificial
<220> FEATURE:
<223> OTHER INFORMATION: Synthetic primer

<400> SEQUENCE: 36
tcctacatct tctgagtttg gtga                                        24

<210> SEQ ID NO 37
<211> LENGTH: 24
<212> TYPE: DNA
<213> ORGANISM: Artificial
<220> FEATURE:
<223> OTHER INFORMATION: Synthetic primer

<400> SEQUENCE: 37
cagaaagcac agcactcgcc ctcc                                        24

<210> SEQ ID NO 38
<211> LENGTH: 23
<212> TYPE: DNA
<213> ORGANISM: Artificial
<220> FEATURE:
<223> OTHER INFORMATION: Synthetic primer

<400> SEQUENCE: 38
catggaaagc ctctgtggat atg                                         23

<210> SEQ ID NO 39
<211> LENGTH: 20
<212> TYPE: DNA
<213> ORGANISM: Artificial
<220> FEATURE:
<223> OTHER INFORMATION: Synthetic primer

<400> SEQUENCE: 39
aagctgcagg cattgatgtg                                             20

<210> SEQ ID NO 40
<211> LENGTH: 24
<212> TYPE: DNA
<213> ORGANISM: Artificial
<220> FEATURE:
<223> OTHER INFORMATION: Synthetic primer

<400> SEQUENCE: 40
ctcatcacgg gccgcctaag gaac                                        24

```
<210> SEQ ID NO 41
<211> LENGTH: 24
<212> TYPE: DNA
<213> ORGANISM: Artificial
<220> FEATURE:
<223> OTHER INFORMATION: Synthetic primer

<400> SEQUENCE: 41
ctttgagaag gatggcaagt atgg                                              24

<210> SEQ ID NO 42
<211> LENGTH: 20
<212> TYPE: DNA
<213> ORGANISM: Artificial
<220> FEATURE:
<223> OTHER INFORMATION: Synthetic primer

<400> SEQUENCE: 42
ttgtaggagg tgccctggaa                                                   20

<210> SEQ ID NO 43
<211> LENGTH: 25
<212> TYPE: DNA
<213> ORGANISM: Artificial
<220> FEATURE:
<223> OTHER INFORMATION: Synthetic primer

<400> SEQUENCE: 43
cagatggaca gccctgcaag ttccc                                             25
```

USE OF 24-NOR-UDCA

This application is a national phase application under 35 U.S.C. 371 of International Application No. PCT/EP2005/052178 filed 12 May 2005. The entire text of the above-referenced disclosure is specifically incorporated by reference herein without disclaimer.

The present invention relates to novel uses of 24-nor-ursodeoxycholic acid (norUDCA).

Ursodeoxycholic acid (UDCA), the naturally occurring bile acid, which can be found in small amounts in the bile and in the blood of humans, is a widely used drug to treat liver diseases, wherein one of the most important indication areas of UDCA is the dissolution of gallstones and the treatment of primary biliary cirrhosis (PBC) and primary sclerosing cholangitis (PSC). UDCA is a naturally occurring bile acid with cytoprotective, membrane stabilizing and anti-apoptotic effects. Furthermore, UDCA lowers serum levels of bilirubin, transaminases and alkaline phosphatase as marker of cholestasis (Trauner & Graziadei 1999, Beuers & Paumgartner 2002).

Studies of UDCA in patients suffering from liver diseases, especially PBC patients, have shown that the administration of UDCA increases the rate of bile flow from the hepatocytes, thereby combating cholestasis and diluting and inhibiting toxic bile acids, which are mainly responsible for the injury to the hepatocytes. Furthermore, UDCA is also able to inhibit the immune response in the liver reducing immunological injury to the bile ducts and the liver. UDCA—as stated above—is regularly used to treat PSC and PBC.

PSC, which affects mainly males, is an inflammatory disease of the bile ducts, which may lead to cholestasis (blockage of bile transport to the gut). The blockage of bile ducts leads to the accumulation of bile acid in the liver and in bile, damages the liver and eventually causes liver failure. Most of the patients suffering from PSC show also a chronic inflammation of the colon (e.g. colitis ulcerosa). The inflammation of the bile duct can affect also the surrounding liver tissue and lead to a cicatrization of the small and large bile ducts, which will cause the constriction of the biliary tract. Consequently, such a constriction leads to a disturbed secretion of bile liquid further damaging the liver. In the course of the disease liver cirrhosis and cholangiocarcinoma may develop. Also PBC is an inflammatory disease of the bile ducts, which affects initially the smaller bile ducts and will finally result in liver cirrhosis. In contrast to PSC, PBC affects mainly female individuals and is not correlated to inflammatory diseases of the colon.

The most efficient method to treat PBC and PSC is the transplantation of the liver. Until now the only promising pharmacological treatment of both diseases involves the use of UDCA. Currently, UDCA is the only drug approved for the treatment of cholestatic liver diseases (Paumgartner & Beuers 2002). UDCA is used in PBC at a dose of 12-15 mg/kg/day (generally 1000-1500 mg) administered orally once or twice a day. This use is approved by the U.S. Food and Drug Administration. Colchicine has been added to UDCA treatment. Colchicine is prescribed at a dose of 0.6 mg twice a day because of its potential anti-inflammatory and anti-fibrotic effects. Several studies have demonstrated mild improvements in liver tests using colchicine. Nevertheless, none found a benefit for the liver histology or survival of PBC patients. Methotrexate, an immune suppressing agent, is another drug which has been tested in PBC. It is administered at a dose of 15 mg per week. In small studies, methotrexate has improved symptoms, liver blood tests and progression of histology when used for several years. However, methotrexate causes severe side effects including bone marrow suppression, worsening of liver disease and potentially fatal pulmonary fibrosis.

UDCA is of limited efficacy in PSC and has not been shown to prolong survival (free of liver transplantation Trauner & Graziadei 1999, Paumgartner & Beuers 2002). Ongoing studies test whether high-dose UDCA may be more effective. Notably, UDCA reduces the risk of colon cancer in patients with PSC and ulcerative colitis. Based on the hypothesis that PSC has an immunologic cause, corticosteroids and other immunosuppressants have been tested. Oral corticosteroids yielded an initial improvement in the biochemical profile. However, lack of evidence for the long term benefit as well as bone demineralization, is an argument against the use of this regimen. Other medications such as azathioprine, cyclosporine, tested in association with corticosteroids and UDCA, have never been evaluated alone in the therapy of PSC. Methotrexate and D-penicillamine were also shown to be ineffective. Therefore, pharmaceutical therapy for PSC still needs to be optimized (Trauner & Graziadei 1999, Beuers & Paumgartner 2002).

Endoscopic treatment in PSC patients with symptomatic dominant strictures, gallstones or debris is considered to be a valuable option in addition to medical treatment. PSC patients undergoing endoscopic treatment had an increased survival, which was much higher than that predicted from survival models.

Orthotopic liver transplantation is an effective therapy for PSC and so far the only life-saving option for the end-stage disease. Following transplantation, however, PSC tends to recur in 15-30% of patients, and there is also a high recurrence rate of biliary strictures, chronic rejection, and reflux cholangitis. Unfortunately, use of immunosuppressants does not improve survival and recurrence of the disease. Thus, an urgent need exists for effective drug treatment preventing disease progression of PSC as well as recurrence after liver transplantation (Trauner & Graziadei 1999, Beuers & Paumgartner 2002).

Although UDCA, which is well tolerated with the exception of rare episodes of diarrhea and prurigo (Trauner & Graziadei 1999, Beuers & Paumgartner 2002), is predominantly used to treat cholestatic liver diseases, the efficacy of UDCA in PSC and in patients with liver diseases like progressive familial intrahepatic cholestasis type 3 is very limited (Trauner & Graziadei 1999, Jacquemin, Hermans, et al. 1997, Jacquemin 2000, Ismail, Kalicinski, et al. 1999).

In the EP 0 652 773 B1 the use of nor- and homo-bile acids derivatives, optionally conjugated with taurine, glycine or alanine, as absorption enhancers for medicaments by the enteral or other non-perenteral routes is described. These derivatives show lipohilic and detergent properties and are not metabolized by the intestinal bacterial flora.

The EP 0 624 595 B1 discloses dimeric nor-derivatives of bile acids for the use in a medicament, especially suited for the treatment of hyperlipidemia. The substances disclosed therein consist of two single bile acid derivatives, which are covalently linked to each other.

U.S. Pat. No. 4,892,868 discloses 22-Methyl-nor-ursodeoxycholic acid and 23-Methyl-ursodeoxycholic acid to be used to treat disorders of the hepatobiliary function, with particular reference to cholesterol metabolism and bile production (e.g. for the treatment of cholestasis).

It is an object of the present invention to provide alternative pharmaceuticals for the treatment of liver diseases, preferably chronic liver diseases, which are more effective than known drugs like ursodeoxycholic acid and show less side effects than methotrexate.

Therefore, the present invention relates to the use of 24-nor-ursodeoxycholic acid and/or pharmaceutical acceptable salts and esters thereof for the manufacture of a drug for the treatment and/or the prevention of liver diseases, preferably chronic liver diseases.

It surprisingly turned out that a medicament or pharmaceutical composition comprising 24-nor-ursodeoxycholic acid, a side chain-shortened $C_{23}$ analogue of the naturally occurring $C_{24}$ bile acid ursodeoxycholic acid (UDCA), and/or pharmaceutical acceptable salts and esters thereof can be successfully employed for the treatment of various liver diseases, because those analogues influence the physiological properties of bile acids (Hofmann 1999, Schmassmann, Hofmann, et al. 1990, Yoon, Hagey, et al. 1986, Cohen, Hofmann, et al. 1986). Although both substances are structurally very similar both substances show different characteristics when administered to mammals (see e.g. Yoon Y B, Hagey L R, et al., 1986).

24-nor-ursodeoxycholic acid and salts and esters thereof lead to the induction of biliary bicarbonate secretion, which dilutes the toxic biliary content and protects bile duct epithelial cells against oxidative stress since bicarbonate is a potent scavenger for reactive oxygen species. This leads to the reconstitution of the cholangiocyte barrier function and will stop ongoing pericholangitis and subsequent periductal fibrosis by minimizing bile duct epithelial cell injury from the bile duct lumen. Furthermore, 24-nor-ursodeoxycholic acid and salts and esters thereof turned out to have also anti-inflammatory and anti-fibrotic effects.

In contrast to 24-nor-deoxycholic acid and salts and esters thereof, ursodeoxycholic acid improves only periductal fibrosis of lobular bile ducts and increases serum alanine aminotrans-ferase (ALT) levels and induces bile infarcts. However, ursodeoxycholic acid does not improve small duct disease. The divergent effects of both bile acids in regard to liver injury may be related to the differences in the level of bile secretion i.e. that 24-nor-ursodeoxycholic acid and salts and esters thereof stimulate primarily ductular secretion whereas ursodeoxycholic acid stimulates canalicular bile secretion upstream of the affected ducts.

The administration of 24-nor-deoxycholic acid and salts and esters thereof induces bile acid detoxification via hydroxylation, sulfation and glucuronidation resulting in better water soluble and therefore less toxic bile acid metabolites, which dilute toxic bile acids in ductular bile and induce a ductular bicarbonate-rich choleresis reducing oxidative stress.

The generation of a bicarbonate rich choleresis by 24-nor-ursodeoxycholic acid and salts and esters thereof has also therapeutic implications in human cholangiopathies (e.g. PSC, PBC, chronic liver graft rejection, non-suppurative destructive cholangitis), as cholehepatic shunting results in a continuing flux of molecules across the biliary ductular epithelium which helps altered bile ducts to better handle toxic/oxidative stress. For example, sulindac, a NSAID that also undergoes cholehepatic shunting in humans, has been shown to improve liver enzymes in PBC patients with incomplete response to UDCA treatment.

Methods for the preparation of 24-nor-ursodeoxycholic acid and salts and esters thereof are known to the person skilled in the art and can preferably be prepared by a method as described in Schteingart C D and Hofmann A F (J. Lip. Res. 29 (1988):1387-1395).

Of course, the drug according to the present invention can be used in humans as well as in mammals (e.g. swine, horse, primates, cattle, cat, dog).

The liver disease to be treated by a drug according to the present invention is a cholestatic liver disease, preferably primary sclerosing cholangitis (PSC), primary biliary cirrhosis (PBC) or progressive familial intrahepatic cholestasis, in particular progressive familial intrahepatic cholestasis type 1, 2 and 3, cystic fibrosis, drug-induced cholestasis or a noncholestatic liver disease such as chronic viral hepatitis (B,C, D), alcoholic and non-alcoholic steatohepatitis, autoimmune hepatitis, hemochromatosis, Wilson disease and alpha-1-antitrypsin deficiency. Furthermore a drug comprising 24-nor-deoxycholic acid and salts and esters thereof can be used for the prevention/chemoprevention of liver carcinoma, preferably hepatocellular carcinoma and cholangiocarcinoma. Also chronic liver graft rejection and non-suppurative destructive cholangitis may be treated by said drug. Especially diseases which are a result or result in a bile duct injury can be treated by a drug comprising 24-nor-ursodeoxycholic acid and salts and esters thereof.

Non-steroidal anti-inflammatory drug (NSAID) like ibuprofen reduce portal and lobular inflammation in the liver (which will lead to periductal fibrosis and ductular proliferation) and the formation of hepatocellular carcinoma (HCC) (Pikarsky, Porat, et al. 2004). Since 24-nor-ursodeoxycholic acid and salts and esters thereof exhibit also anti-inflammatory properties, 24-nor-ursodeoxycholic acid may be used alone or in combination with other anti-inflammatory drugs, like NSAIDs (e.g. ibuprofen, sulindac (Bolder, Trang, et al. 1999)).

According to another preferred embodiment of the present invention the liver disease is primary sclerosing cholangitis (PSC). Furthermore, the liver disease is preferably primary biliary cirrhosis (PBC). 24-nor-ursodeoxycholic acid and salts and esters thereof can be used especially to treat PSC and PBC.

A drug comprising 24-nor-ursodeoxycholic acid and/or salts or esters thereof may especially be used for the treatment of primary sclerosing cholangitis (PSC) and primary biliary cirrhosis (PBC).

According to a preferred embodiment of the present invention 24-nor-ursodeoxycholic acid and salts and esters thereof can be formulated for oral or intravenous administration, wherein these formulations further comprise pharmaceutically acceptable carriers, adjuvants, excipients and/or vehicles. Solid dosage forms for oral administration can include tablets, preferably effervescent or chewable tablets, capsules, pills, powders and granules. In such solid dosage forms, 24-nor-ursodeoxycholic acid can be admixed with regularly used substances like sucrose, mannitol, sorbitol, starch and starch derivatives, lactose, lubricating agents (e.g. magnesium stearate), disintegrants and buffering agents. Tablets and pills can also be prepared with enteric coatings in order to prevent that 24-nor-ursodeoxycholic acid is affected by the stomach acids and enzymes. As immediate release tablets, these compositions may further comprise microcrystalline cellulose and/or dicalcium phosphate.

Liquid dosage forms for oral administration can include pharmaceutically acceptable emulsions, solutions, suspensions and syrups containing inert diluents commonly used in the art, such as water. These dosage forms may contain microcrystalline cellulose for imparting bulk, alginic acid or sodium alginate as a suspending agent, methylcellulose as a viscosity enhancer, and sweetners/flavoring agents. When administered by nasal aerosol or inhalation, the compositions according to the present invention may be prepared as solutions in saline, employing benzyl alcohol or other suitable preservatives, absorption promoters to enhance bioavailability, fluorocarbons and/or other solubilizing or dispersing agents.

Suppositories for rectal administration of 24-nor-ursodeoxycholic acid can be prepared by mixing the compounds or compositions with a suitable nonirritating excipient such as cocoa butter and polyethylene glycols which are solid at room temperature but liquid at rectal temperature, such that they will melt in the rectum and release 24-nor-ursodeoxycholic acid and optionally other active compounds present in said suppositories.

Injectable preparations, for example sterile injectable aqueous or oleaginous suspensions, can be formulated according to the known art using suitable dispersing agents, wetting agents and/or suspending agents. The sterile injectable preparation can also be a sterile injectable solution or suspension in a nontoxic parenterally acceptable diluent or solvent. Among the acceptable vehicles and solvents that can be used are water and isotonic sodium chloride solution. Sterile fixed oils are also conventionally used as a solvent or suspending medium.

According to the present invention the dosage forms comprising 24-nor-ursodeoxycholic acid can further include conventional excipients, preferably pharmaceutically acceptable organic or inorganic carrier substances which do not react with the active compound. Suitable pharmaceutically acceptable carriers include, for instance, water, salt solutions, alcohol, oils, preferably vegetable oils, polyethylene glycols, gelatin, lactose, amylose, magnesium stearate, surfactants, perfume oil, fatty acid monoglycerides and diglycerides, petroethral fatty acid esters, hydroxymethyl-cellulose, polyvinylpyrrolidone and the like. The pharmaceutical preparations can be sterilized and if desired, mixed with auxiliary agents, like lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants.

Various delivery systems are known and can be used to administer 24-nor-ursodeoxycholic acid, including, for example, encapsulation in liposomes, emulsions, microparticles, microcapsules and microgranules (e.g. EP 1 317 925). The required dosage can be administered as a single unit or in a sustained release form.

The bioavailability of 24-nor-ursodeoxycholic acid can be enhanced by micronization of the formulations using conventional techniques such as grinding, milling and spray drying in the presence of suitable excipients or agents such as phospholipids or surfactants.

According to the invention 24-nor-ursodeoxycholic acid can be formulated in a pharmaceutically acceptable salt or ester form. Pharmaceutically acceptable salts of 24-nor-ursodeoxycholic acid include preferably metal salts, in particular alkali metal salts, or other pharmaceutically acceptable salts. Suitable pharmaceutically acceptable acid addition salts may be prepared from inorganic acids, like hydrochloric, hydrobromic, hydroiodic, nitric, carbonic, sulfuric and phosphoric acid, or organic acids, like aliphatic, cycloaliphatic, aromatic, heterocyclic, carboxylic and sulfonic classes of organic acids, such as, formic, acetic, propionic, succinic, glycolic, gluconic, lactic, malic, tartaric, citric, ascorbic, glucuronic, maleic, fumaric, pyruvic, aspartic, glutamic, benzoic, ethanesulfonic, anthranilic, mandelic, mesylic, salicylic, p-hydroxybenzoic, phenylacetic, methanesulfonic, benzenesulfonic, pantothenic, toluenesulfonic, 2-hydroxyethanesulfonic, algenic, sulfanilic, stearic, p-hydroxybutyric, cyclohexylaminosulfonic, galactaric and galacturonic acid and the like. Pharmaceutically acceptable base addition salts include metallic salts made from lithium, aluminum, calcium, magnesium, potassium, sodium and zinc or organic salts made from primary, secondary and tertiary amines and cyclic amines. All 24-nor-ursodeoxycholic acid salts can be prepared by methods known in the state of the art (e.g. by reacting 24-nor-ursodeoxycholic acid with the appropriate acid or base). 24-nor-ursodeoxycholic acid esters are non-toxic esters, preferably alkyl esters such as methyl, ethyl, propyl, isopropyl, butyl, isobutyl or pentyl esters, or aryl esters. Esterification of carboxylic acids, such as 24-nor-ursodeoxycholic acid, is performed by a variety of conventional procedures, including reacting the carboxylic group with an appropriate alcohol. These reactions are known to the person skilled in the art.

Methods for the manufacture of a drug according to the present invention comprising 24-nor-ursodeoxycholic acid and formulated for the administration as outlined herein can be found, for instance, in the "Handbook of Pharmaceutical Manufacturing Formulations" (Sarfaraz K Niazi, CRC Press LLC, 2004).

The drug comprises preferably an effective amount of 24-nor-ursodeoxycholic acid and a pharmaceutically acceptable carrier and/or excipient.

According to a preferred embodiment of the present invention the medicament comprises 10 to 8000 mg, preferably 25 to 5000 mg, more preferably 50 to 1500 mg, in particular 250-500 mg, of 24-nor-ursodeoxycholic acid.

On average 24-nor-ursodeoxycholic acid and/or pharmaceutical acceptable salts and esters thereof may preferably be administered to a patient in an amount of 25 mg to 5 g, preferably 100 mg to 2.5 g, in particular 800 mg to 1.5 g per day. However, 1 g of 24-nor-ursodeoxycholic acid and/or pharmaceutical acceptable salts and esters thereof is most preferably administered to a patient. It is further noted that 24-nor-ursodeoxycholic acid and/or pharmaceutical acceptable salts and esters thereof may be administered to an individual in 1-100 mg/kg/d, preferably 5-50 mg/kg/d, more preferably 10-25 mg/kg/d, in particular 12-15 mg/kg/d. Said amounts are administered at once or preferably in more than one dose (at least 2, 3, 4, 5 or 10 doses) per day. The drug or the pharmaceutical composition according to the present invention may be administered for more than one week, preferably more than four weeks, more preferably more than six months, most preferably more than one year, in particular life-long.

24-nor-ursodeoxycholic acid can be administered not only in combination with pharmaceutically acceptable carriers and in dosage forms as described herein, but, of course, also in combination with one or more additional active ingredients (e.g. ursodeoxycholic acid, NSAID, like sulindac and ibuprofen) which are also known to be effective against the same or a similar disease to be treated (e.g. ursodeoxycholic acid) or against another disease, which may be preferably a result of a liver disease.

According to the present invention not only nor-UDCA can be used for the treatment and/or prevention of liver diseases as disclosed herein, but also other bile acids having any other side chain modification that prevents efficient N-acyl amidation (may be analysed by any suitable method known in the art, especially by the methods described by Johnson, M., et al. Anal. Biochem., (1989) 182:360-365; Yoon, Hagey, et al. 1986) such as, but not limited to, decreased length (e.g. nor and dinor-bile acids), addition of an alkyl group (especially methyl-, ethyl-, propyl-, butyl-, pentyl- and hexyl-groups) at the alpha or beta carbon. These UDCA-derivatives result in pharmaceutical and therapeutic properties similar to those of nor-UDCA, specifically for the treatment and prevention of PBC and PSC.

The present invention is further illustrated by the following figures and example without being restricted thereto.

FIG. 1. norUDCA Cures Sclerosing Cholangitis in Mdr2$^{-/-}$ Mice. (A) Liver histology (H&E staining) in control diet-fed Mdr2$^{-/-}$ mice (KO), UDCA-fed Mdr2$^{-/-}$ mice (KO+UDCA), and norUDCA-fed Mdr2$^{-/-}$ mice (KO+norUDCA) (Magnification ×10). Pronounced large bile duct disease in KO (arrow heads) which is significantly reduced in KO+UDCA (arrow heads) and absent in KO+norUDCA. (B) Sclerosing cholangitis in KO with periductal fibrosis, alterated bile duct epithelial cells and mixed inflammatory infiltrate. This features are ameliorated in KO+UDCA and absent in KO+norUDCA (Magnification ×40). (C) Sirius red staining showing significant fibrosis with periductal collagen fibers (red) in KO. Moderate reduction of fibrosis in KO+UDCA and even more pronounced reduction in KO+norUDCA (Magnification for b, c×40); bd, bile duct.

Figure 2:
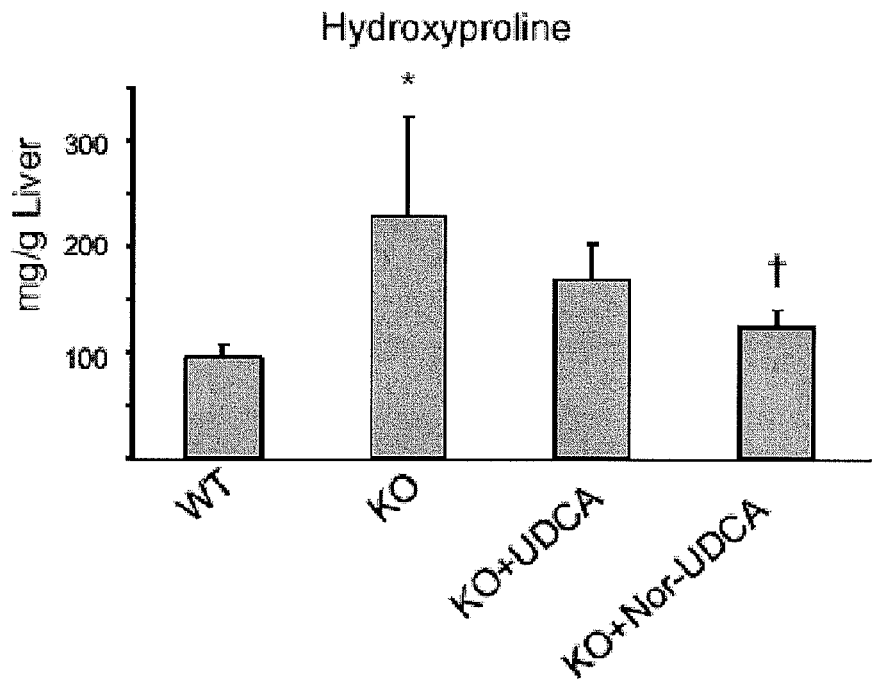

FIG. 2. norUDCA significantly reduces hepatic hydroxyproline content in Mdr2$^{-/-}$. Hepatic hydroxyproline content in wild type (WT), control diet-fed Mdr2$^{-/-}$ mice (KO), UDCA-fed Mdr2$^{-/-}$ mice (KO+UDCA), and Nor-UDCA-fed Mdr2$^{-/-}$ mice (KO+norUDCA). Hepatic hydroxyprolin content is significantly increased in KO compared to WT and reduced to baseline levels in KO+norUDCA. Values are mean±SEM from n=5 per group. p<0.05, WT vs. KO; KO vs. KO+norUDCA.

Figure 3:
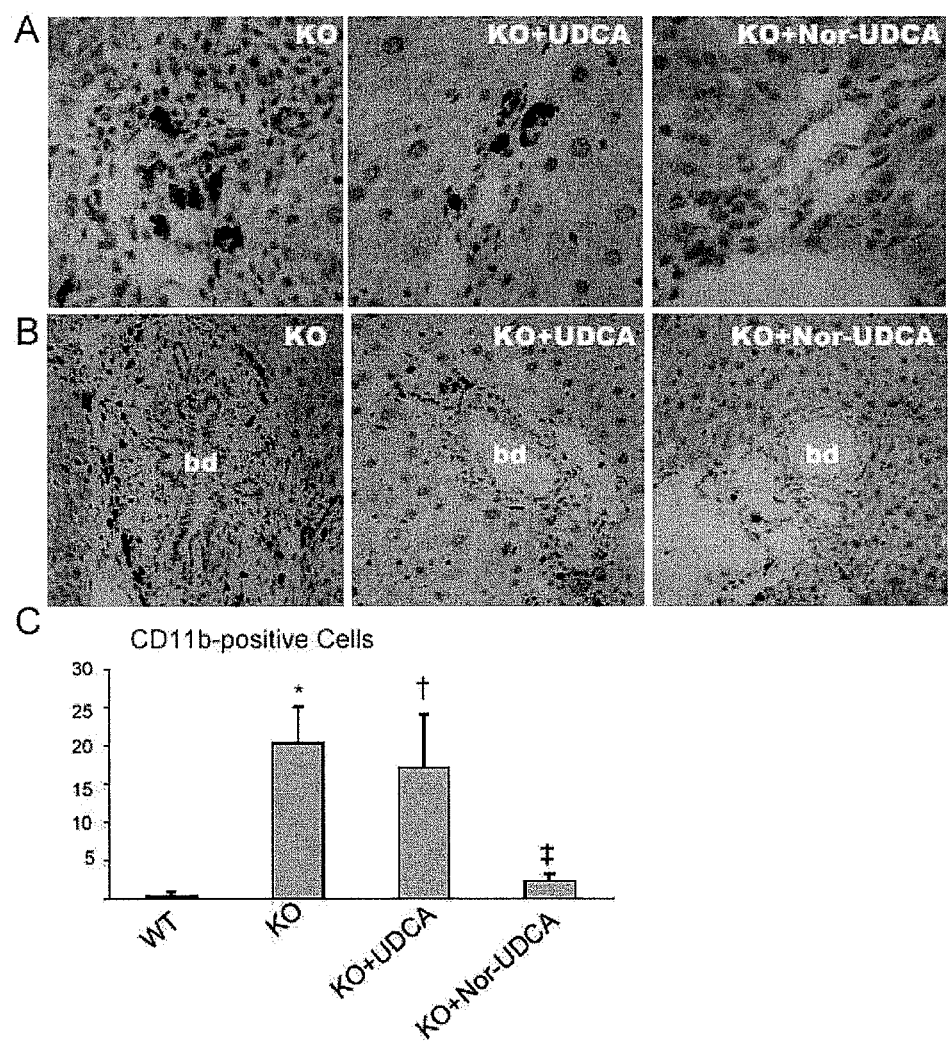

FIG. 3. norUDCA significantly reduces portal neutrophils infiltration/extravasation in Mdr2$^{-/-}$. Immunohistochemistry for CD11b (red, staining neutrophils) in control diet-fed Mdr2$^{-/-}$ mouse (KO), UDCA-fed Mdr2$^{-/-}$ mouse (KO+UDCA), and norUDCA-fed Mdr2$^{-/-}$ mouse (KO+norUDCA) of (A) interlobular and (B) lobular bile ducts. (C) Quantification of CD11b-positive cells per 20 portal fields. norUDCA significantly reduces the number of CD11b-positive cells in Mdr2$^{-/-}$. Values are mean±SEM from n=3 per group. p<0.05, FIG. 4. norUDCA inhibits portal vascular cell adhesion molecule (VCAM) expression in Mdr2$^{-/-}$ mice. Immunohistochemistry for VCAM (red) in interlobular (A) and lobular (B) ile ducts of control diet-fed Mdr2$^{-/-}$ mouse (KO), UDCA-fed Mdr2$^{-/-}$ mouse (KO+UDCA), and norUDCA-fed Mdr2$^{-/-}$ mouse (KO+norUDCA). (A) No obvious difference in portal VCAM expression between KO and KO+UDCA whereas KO+norUDCA show significantly lower expression in bile duct proliferates. (B) At the level of lobular bile ducts both UDCA and norUDCA reduce cholangiocellular VCAM expression.

FIG. 5. norUDCA inhibits proliferation of hepatocytes and cholangiocytes in Mdr2$^{-/-}$ mice. Immunohistochemistry for Ki-67 (red) in hepatocytes (A) and cholangiocytes (B) in control diet-fed Mdr2$^{-/-}$ mouse (KO), UDCA-fed Mdr2$^{-/-}$ mouse (KO+UDCA), and norUDCA-fed Mdr2$^{-/-}$ mouse (KO+norUDCA). (A) Numerous Ki-67 positive hepatocytes in KO and KO+UDCA and scattered positive nuclei in KO+norUDCA. (B) Numerous Ki-67 positive cholangiocytes in KO, few positive cholangiocytes (arrow heads) in KO+UDCA and KO+norUDCA, respectively. (C) Number of Ki-67 positive hepatocytes per 30 HPFs and (D) number of Ki-67 positive cholangiocytes per 20 portal fields. Only norUDCA significantly reduces the number proliferating hepatocytes and cholangiocytes. Values are mean±SEM from n=3 per group. p<0.05,*WT vs. KO; † WT vs. KO+UDCA; ‡KO vs. KO+norUDCA.

Figure 6:
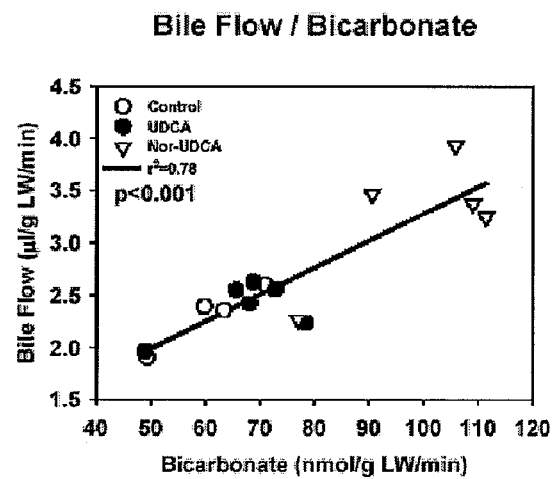

FIG. 6. Positive correlation between biliary bicarbonate output and bile flow in Mdr2$^{-/-}$. Biliary bicarbonate output was plotted against bile flow in control diet-fed Mdr2$^{-/-}$ mice (Control, open circles), UDCA-fed Mdr2$^{-/-}$ mice (UDCA, open triangles), and NorUDCA-fed Mdr2$^{-/-}$ mice (norUDCA, closed circles). Note the positive correlation between bicarbonate output and bile flow as well as the clustering of Nor-UDCA-treated animals showing the highest bicarbonate output in the upper right.

Figure 7:
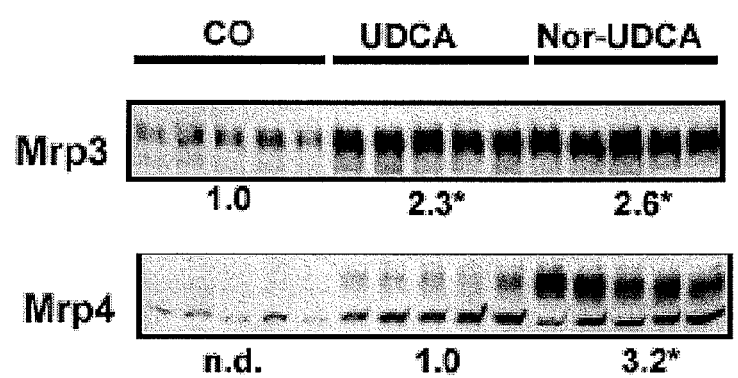

FIG. 7. Suggested therapeutic mechanisms of norUDCA in Mdr2$^{-/-}$ mice. norUDCA is taken up by hepatocytes and secreted into canaliculi and bile ducts where it is taken up by cholangiocytes leading to ductular bicarbonate secretion. norUDCA is secreted back into the peribiliary plexus and shunted back to the hepatocytes (cholehepatic shunting). NorUDCA induces expression of Sult2a1 etc. and Mrp3 and Mrp4 which detoxifies bile salts and makes them amenable for renal elimination.

FIG. 8. Chemical structure of norUDCA (3-alpha,7-alpha-dihydroxy-24-nor-5-beta-cholan-23-oic acid).

EXAMPLE 1

Mice with targeted disruption of the Mdr2 (Abcb4) gene encoding a canalicular phospholipid flippase develop sclerosing cholangitis with macroscopic and microscopic features closely resembling those seen in human sclerosing cholangitis (e.g. primary sclerosing cholangitis, PSC) (Fickert, Zollner, et al. 2002, Fickert, Fuchsbichler, et al. 2004). Bile duct injury in these mice is linked to defective biliary phospholipids secretion resulting in an increased concentration of free non-micellar bile acids which subsequently cause bile duct epithelial cell (cholangiocyte) injury, pericholangitis, periductal fibrosis with ductular proliferation and finally sclerosing cholangitis (Fickert, Fuchsbichler, et al. 2004, Lammert, Wang, et al. 2004). In addition to the opportunity to study novel treatment strategies for PSC this model may be relevant for testing therapies for the wide spectrum of human liver diseases resulting from MDR3 mutations (the human orthologue of Mdr2) ranging from neonatal cholestasis to adult liver disease (Jansen & Sturm 2003).

Currently, UDCA is the only drug approved for the treatment of cholestatic liver diseases (Paumgartner & Beuers 2002). However the efficacy of UDCA in PSC and in patients with liver diseases due to MDR3 mutations (e.g. progressive familial intrahepatic cholestasis type 3) is limited (Trauner & Graziadei 1999, Jacquemin, Hermans, et al. 1997, Jacquemin 2000, Ismail, Kalicinski, et al. 1999). Side-chain shortening of UDCA could increase its therapeutic efficacy since this modification significantly influences the physiological properties of bile acids (Hofmann 1999, Schmassmann, Hofmann, et al. 1990, Yoon, Hagey, et al. 1986, Cohen, Hofmann, et al. 1986). norUDCA, a side chain-shortened $C_{23}$ analogue of UDCA, is a potent choleretic agent in different rodents (e.g. hamster, rat, guinea pig) undergoing extensive cholehepatic shunting and inducing biliary bicarbonate secretion at the bile duct level (Yoon, Hagey, et al. 1986, Cohen, Hofmann, et al. 1986). In contrast to UDCA, the effects of norUDCA have never been studied in cholestasis. To test the hypothesis that cholehepatic shunting of a non-toxic bile acid may be beneficial in the treatment of cholangiopathies investigated the effects of norUDCA in Mdr2$^{-/-}$ mice as a model of sclerosing cholangitis (Fickert, Fuchsbichler, et al. 2004). In this example the positive effects of norUDCA in the treatment for human liver diseases caused by MDR3 mutations and human cholangiopathies such as sclerosing cholangitis (e.g. PSC) are examined.

1.1. Materials and Methods

1.1.1. Animal Experiments.

Mdr2$^{-/-}$ mice (FVB/N background) were obtained from Jackson Laboratory (The Jackson Laboratory, Bar Harbor, Me., USA). Mice were housed with a 12:12-hour light-dark cycle and permitted ad libitum consumption of water and a standard mouse diet (Sniff, Soest, Germany).

1.1.2. Bile Acid Feeding in Mdr2$^{-/-}$ Mice.

Two months-old Mdr2$^{-/-}$ (a time point when sclerosing cholangitis is already fully established in these animals (Fickert, Zollner, et al. 2002) were either fed a diet supplemented with norUDCA (0.5%, w/w) or UDCA as a clinical comparator (0.5%, w/w) for 4 weeks and compared to standard-diet-fed Mdr2$^{-/-}$ and wild type controls.

1.1.3. Liver Histology.

For conventional light microscopy, livers were fixed in 4% neutral buffered formaldehyde solution and embedded in paraffin. Sections (4 µm thick) were stained with H&E and Sirius red stain, respectively. The sections were coded and examined by a pathologist (H. D.) unaware of the animals' treatment.

1.1.4. Routine Serum Biochemistry.

Serum samples were stored at −70° C. until analysis of alanine transaminase (ALT) and alkaline phosphatase (AP) by routine clinical chemistry performed on a Hitachi 717 analyzer (Boehringer Mannheim, Mannheim, Germany). For determination of total serum bile acid levels, a commercial 3-alpha-hydroxysteroid dehydrogenase assay (Ecoline S+; DiaSys, Holzheim, Germany) was used.

1.1.5. Immunohistochemistry for Alpha-SMA.

Immunohistochemistry for alpha-SMA was performed on microwave treated (0.01 mmol/L citrate buffer pH 6.0) paraffin sections (4 µm thick) using the monoclonal mouse anti alpha-SMA (dilution 1:500, Sigma, St Louis, Mo.). Binding of the antibody was detected using the ABC system (Dako, Glostrup, Denmark) using β-amino-9-ethyl-carbazole (AEC; Dako) as substrate.

1.1.6. Immunohistochemistry for Proliferation Marker Ki-67.

Immunohistochemistry for Ki-67 was performed on microwave-treated (0.01 mmol/L citrate buffer pH 6.0) paraffin sections (4 µm thick) using a polyclonal rabbit anti-Ki-67 antibody (dilution 1:750, Novocastra, Newcastle upon Tyne, UK). Binding of the antibody was detected using the ABC system (Dako) using AEC (Dako) as substrate. Number of proliferating hepatocytes was calculated by counting positive nuclei in 30 high power fields in sections of 3 animals in each group. Number of proliferating bile duct epithelial cells was calculated by counting positive nuclei in 20 portal fields in sections of 3 animals in each group.

1.1.7. Immunohistochemistry for Neutrophils Marker CD-11b.

To quantify neutrophils CD 11b-positive cells were detected as described previously (Fickert, Fuchsbichler, et al. 2004) with the modification that binding of the antibody was detected using the ABC system (Dako) using AEC (Dako) as substrate. Number of neutrophils was calculated by counting positive cells in 20 portal fields in sections of 3 animals in each group.

1.1.8. Immunohistochemistry for Vascular Cell Adhesion Molecule (VCAM).

Immunohistochemistry for VCAM was performed on acetone fixed cryosections using the monoclonal rat anti CD106 (VCAM-1, dilution 1:30, PharMingen, San Diego, Calif., USA) and binding of the antibody was detected using the ABC system (Dako) using AEC (Dako) as substrate.

1.1.9. Immunohistochemistry for 4-Hydroxynonenal-Protein Adducts.

Liver sections were deparaffinized and then incubated with Immunopure peroxidase suppressor (Pierce, Rockford, Ill.) for 30 min and then protein block (DAKO, Carpenteria, Calif.) for 2 h. This was followed by overnight incubation with the primary anti-4-hydroxynonenal antibody (Calbiochem, San Diego, Calif.) at room temperature and binding of the antibody was detected using the ABC system (Dako) with AEC (Dako) as substrate.

1.1.10. Determination of Hepatic Hydroxyproline Content.

To quantify liver fibrosis in our model hepatic hydroxyproline content was determined. The right liver lobe was homogenized in 6-normal HCl (200 mg liver tissue/4 ml HCl) and hydrolyzed at 110° C. for 16 h. After filtration 50 µl were added to 450 µl 2.2% NaOH dissolved in citrate-acetate buffer (50 g citric acid×H$_2$O, 12 ml acidic acid, 120 g sodium acetate×3H$_2$O, 34 g NaOH ad 1 liter distilled water; pH 6.0). After adding 250 µl perchloric acid and 12 min incubation at room temperature 250 µl p-dimethylaminobenzaldehyde solution was added and incubated at 60° C. for 20 min. Hydroxyproline content was measured at 565 nm using a hydroxyproline standard curve.

1.1.11. mRNA Analysis and PCR of Key Fibrosis Genes.

RNA isolation, cDNA synthesis and Taqman® real time PCR were performed as described previously (Wagner, Fickert, et al. 2003). The following primers and 5' FAM, 3' TAMRA labeled probes were used: Col1a1 fwd: caatgcaatgaagaactggactgt (Seq ID No. 35), Col1a1 rev: tcctacatcttctgagtttggtga (Seq ID No. 36) and Col1a1 probe: cagaaagcacagcactcgccctcc (Seq ID No. 37); TIMP-1 fwd: catggaaagcctctgtggatatg (Seq ID No. 38), TIMP-1 rev: aagctgcaggcattgatgtg (Seq ID No. 39) and TIMP-1 probe: ctcatcacgggccgcctaaggaac (Seq ID No. 40); MMP-2 fwd: ctttgagaaggatggcaagtatgg (Seq ID No. 41), MMP-2 rev: ttgtaggaggtgccctggaa (Seq ID No. 42) and MMP-2 probe: cagatggacagccctgcaagttccc (Seq ID No. 43).

1.1.12. Bile Flow Measurement.

Bile flow was determined gravimetrically and normalized to liver weight as described previously (Fickert, Zollner, et al. 2001). Biliary phospholipids concentration was determined using a commercially available kit (Phospholipid B; Wako, Neuss, Germany) according to the manufacture's instructions. Biliary cholesterol concentration was determined using a commercial available kit (Cholesterol liquicolor; Human, Wiesbaden, Germany) according to the manufacture's instructions. Biliary gluthathione (GSH) concentration was determined after protein precipitation in 5% metaphosphoric acid using the Glutathione Assay Kit (Calbiochem, San Diego, US) according to the manufacturer's instructions. Biliary bile acid concentration was analyzed using a 3-alpha-hydroxysteroid dehydrogenase assay (Ecoline St, DiaSys) according to the manufacturer's instructions.

1.1.13. Statistical Analysis.

Data are reported as arithmetic means+/−SD. 4 to 6 animals were studied in each group. Statistical analysis was performed using Student's t-test when appropriate or ANOVA with Bonferroni post testing when three or more groups were compared. A p-value <0.05 was considered significant.

1.2. Results

1.2.1. norUDCA Significantly Improves Liver Injury, Reduces Fibrosis, and Cures Sclerosing Cholangitis in Mdr2$^{-/-}$ Mice.

Serum ALT and AP levels (as biochemical markers for liver injury and cholestasis) were significantly elevated in standard diet-fed Mdr2$^{-/-}$ compared to wild type controls (Table 1).

TABLE 1

Serum Biochemistry and Bile Acid Levels under various experimental conditions.

| | ALT (U/L) | AP (U/L) | Bili |
|---|---|---|---|
| WT | 71 ± 19 | 92 ± 13 | 0.09 ± 0.03 |
| KO | 405 ± 187 | 235 ± 55 | 0.32 ± 0.11 |
| KO + UDCA | 576 ± 175* | 399 ± 73* | 0.55 ± 0.19 |
| KO + Nor-UDCA | 165 ± 23*# | 162 ± 25*# | 0.23 ± 0.2# |

NOTE.
Values are expressed as mean ± SD from n = 5 per group. ALT, alanine transaminase; AP, alkaline phosphatase; SBA, serum bile acids; WT, wild type mice; KO, Mdr2 knock-out mice; KO + UDCA, UDCA-fed Mdr2 knock-out mice; KO + norUDCA, norUDCA-fed Mdr2 knock-out mice.
*$p < 0.05$, KO vs. KO + UDCA and KO vs. KO + norUDCA (ANOVA with Bonferroni post-testing)
$p < 0.05$, KO + UDCA vs. KO + norUDCA (ANOVA with Bonferroni post-testing)

norUDCA significantly improved serum ALT and AP levels compared to standard diet-fed Mdr2$^{-/-}$ (Table 1). In parallel standard diet-fed Mdr2$^{-/-}$ displayed pronounced sclerosing cholangitis (FIG. 1) with ductular proliferation and liver fibrosis reflected by significantly elevated hepatic hydroxyproline content (FIG. 2). norUDCA-fed Mdr2$^{-/-}$ showed regular large- and medium-sized bile ducts with no or only modest periductal fibrosis (FIG. 1); ductular proliferation was virtually absent (not shown). In line with this histological changes, norUDCA significantly reduced hepatic hydroxyproline content in Mdr2$^{-/-}$ (FIG. 2) which was paralleled by a significant reduction in hepatic collagen 1 and 3 mRNA expression (Table 2).

UDCA treatment in Mdr2$^{-/-}$ as a clinical comparator and current standard treatment of cholestatic liver diseases (including PSC) were studied simultaneously. In contrast to norUDCA, UDCA significantly increased ALT and AP activity in Mdr2$^{-/-}$ (Table 1) and 2 out of 5 animals showed bile infarcts in line with previous observations (Fickert, Zollner, et al. 2002). UDCA appeared to reduce periductal fibrosis of lobular and interlobular bile ducts (FIG. 1) but showed only a trend for lower hepatic hydroxyproline content without reaching statistical significance (FIG. 2). These findings clearly indicate that norUDCA (but not UDCA) significantly reduces liver injury, pericholangitis, and periductal fibrosis in Mdr2$^{-/-}$ finally leading to healing of sclerosing cholangitis.

1.2.2. norUDCA Reduces Inflammation, Oxidative Stress and Cell Proliferation in Mdr2$^{-/-}$ Mice.

Figure 4:
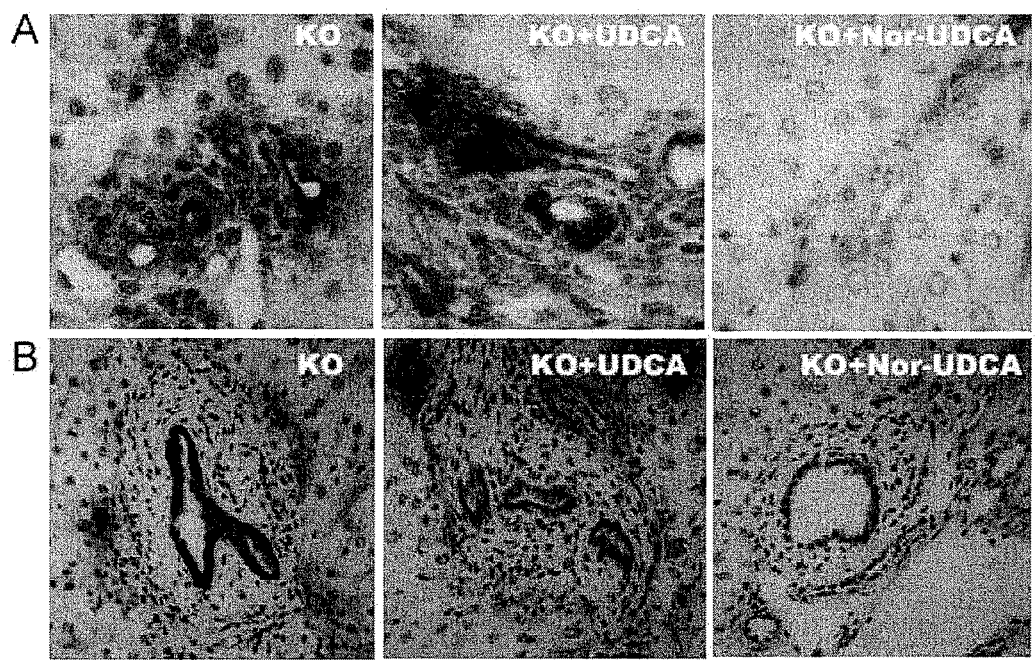

Since portal inflammation may represent the main trigger for periductal fibrosis in Mdr2$^{-/-}$ (Pikarsky, Porat, et al. 2004) the reduction portal inflammation with norUDCA was analysed. Control diet-fed Mdr2$^{-/-}$ had a significantly elevated number of portal neutrophils compared to wild type controls (FIG. 3). norUDCA also improved pericholangitis in Mdr2$^{-/-}$ as reflected by a significantly reduced number of portal neutrophils compared to standard diet-fed Mdr2$^{-/-}$ (FIG. 3). These apparent anti-inflammatory effects of norUDCA were paralleled by the significantly lower VCAM expression in the bile duct epithelial cells of interlobular and lobular bile ducts of norUDCA-fed Mdr2$^{-/-}$ (FIG. 4). Since it was previously shown that inflammation triggers also proliferation in livers of Mdr2$^{-/-}$ (Pikarsky, Porat, et al. 2004) it was tested whether this was affected by norUDCA. Standard diet-fed Mdr2$^{-/-}$ showed a significantly elevated number of Ki-67 positive hepatocytes and cholangiocytes compared to wild type con-

TABLE 2

Real time PCR primer sequences (5'- 3')

| | Forward | Seq ID | Reverse | Seq ID |
|---|---|---|---|---|
| Cyp2b10 | CAATGGGAACGTTGGAAGA | 1 | TGATGCACTGGAAGAGGAAC | 2 |
| Cyp3a11 | CCACCAGTAGCACACTTTCC | 3 | TTCCATCTCCATCACAGTATCA | 4 |
| IL-1β | CTGGTGTGTGACGTTCCCATTA | 5 | CCGACAGCACGAGGCTTT | 6 |
| IL-1R | GCCAGGACCGCTCAGAGA | 7 | TGCCTCGACTGTTAGTCAAGCA | 8 |
| IL-6 | GCCCACCAAGAACGATAGTCA | 9 | GAAGGCAACTGGATGGAAGTCT | 10 |
| MMP3 | CCCACCAAGTCTAACTCTCTGGAA | 11 | GGGTGCTGACTGCATCAAAGA | 12 |
| MIP-2 | CCTCAACGGAAGAACCAAAGAG | 13 | CTCAGACAGCGAGGCACATC | 14 |
| Mrp3 | GGCAGGGCCACACTGAGT | 15 | AGTCCTCAGATGTCAGCCTAGTGA | 16 |
| Mrp4 | TTAGATGGGCCTCTGGTTCT | 17 | GCCCACAATTCCAATTCCAACCTT | 18 |
| i-NOS | ACATCAGGTCGGCCATCACT | 19 | CGTACCGGATGAGCTGTGAATT | 20 |
| Procollagen 1 | GCAGGGTTCCAACGATGTTG | 21 | GCAGCCATCGACTAGGACAGA | 22 |
| Procollagen 3 | GGTGGTTTTCAGTTCAGCTATGG | 23 | CTGGAAAGAAGTCTGAGGAATGC | 24 |
| TGF-beta | TCGACATGGAGCTGGTGAAA | 25 | CTGGCGAGCCTTAGTTTGGA | 26 |
| TNF-alpha | GACCCTCACACTCAGATCATCTTCT | 27 | CCTCCACTTGGTGGTTTGCT | 28 |
| TNF-R1 | TGCACTAAACAGCAGAACCGAG | 29 | TTGCTCAGCCTCATGCACTG | 30 |
| Sult2a1 | GGAAGGACCACGACTCATAAC | 31 | GATTCTTCACAAGGTTTGTGTTACC | 32 |
| Ugt1a1 | TCTGAGCCCTGCATCTATCTG | 33 | CCCCAGAGGCGTTGACATA | 34 | trols (FIG. 5). norUDCA significantly reduced the degree of hepatocyte and bile duct epithelial cell proliferation to nearly wild type control levels (FIG. 5). UDCA had no significant effects on portal inflammation (FIG. 3), VCAM expression (FIG. 4), and proliferation of hepatocytes (FIG. 5). However, UDCA reduced proliferation of bile duct epithelial cells in large bile ducts (FIG. 5). Again, these data indicate that the anti-inflammatory and anti-proliferative effects of norUDCA are superior to UDCA.

1.2.3. norUDCA Induces Biliary Bicarbonate Secretion in $Mdr2^{-/-}$ Mice.

To determine whether bicarbonate rich choleresis resulting from cholehepatic shunting of norUDCA could be responsible for the observed therapeutic effects, bile flow and composition were determined (Table 3).

TABLE 3

Bile flow and biliary excretion of bile acids, cholesterol, phospholipids and glutathione under various experimental conditions.

|  |  | KO $n = 4$ | KO + UDCA $n = 6$ | KO + norUDCA $n = 5$ |
|---|---|---|---|---|
| Bile flow | μL/g/min | 2.3 ± 0.3 | 2.4 ± 0.3 | 3.5 ± 0.3 |
| Bile acids | nmol/g/min | 23.0 ± 5.9 | 37.2 ± 7.6* | 29.5 ± 2.3 |
| Cholesterol | nmol/g/min | 0.2 ± 0.1 | 0.3 ± 0.1 | 0.2 ± 0.04 |
| Phospholipids | nmol/g/min | 0.4 ± 0.1 | 0.3 ± 0.03 | 0.3 ± 0.1 |
| Glutathione | nmol/g/min | 4.6 ± 2.0 | 5.6 ± 1.1 | 5.8 ± 1.2 |
| Bicarbonate | nmol/g/min | 60.9 ± 8.0 | 67.1 ± 10.0 | 98.8 ± 14.6# |

NOTE.
Values are expressed as mean ± SD. KO, Mdr2 knock-out mice; KO + UDCA, UDCA-fed Mdr2 knock-out mice; KO + norUDCA, norUDCA-fed Mdr2 knock-out mice.
*$p < 0.05$, KO vs. KO + UDCA (ANOVA with Bonferroni post-testing)
$p < 0.05$, KO vs. KO + norUDCA (ANOVA with Bonferroni post-testing)

Compared to control diet-fed and UDCA-fed $Mdr2^{-/-}$ norUDCA significantly induced biliary bicarbonate secretion consistent with the concept that norUDCA undergoes relevant cholehepatic shunting in $Mdr2^{-/-}$ (Bolder, Trang, et al. 1999). UDCA but not norUDCA stimulated biliary bile acid excretion. No significant effects on biliary bile acid, cholesterol, phospholipids and glutathione output were observed. These findings show that norUDCA leads to flushing of the injured bile ducts with a bicarbonate-enriched less toxic bile in $Mdr2^{-/-}$.

1.2.4. norUDCA Induces Phase II Detoxification Pathways and Alternative Excretory Routes for Bile Acids in $Mdr2^{-/-}$ Mice.

To test the hypothesis that induction of phase I/II biotransformation pathways and alternative efflux routes for potentially toxic bile acids may also contribute to the observed beneficial effects of norUDCA in $Mdr2^{-/-}$ the expression of key metabolic enzymes (Table 4) and serum, hepatic, and biliary bile acid composition in norUDCA-fed $Mdr2^{-/-}$ was studied.

TABLE 4

Real-time PCR for quantification of relative expression levels of key metabolic enzymes and transport proteins under various experimental conditions.

|  | KO | KO + UDCA | KO + norUDCA |
|---|---|---|---|
| Cyp2b10 | 100 ± 103 | 751 ± 245* | 1294 ± 418*# |
| Cyp3a11 | 100 ± 46 | 246 ± 72* | 241 ± 45* |
| Sult2a1 | n.d. | 100 ± 46 | 24157 ± 14948*# |
| Ugt1a1 | 100 ± 54 | 137 ± 55 | 304 ± 81*# |
| Cyp7a1 | 100 ± 78 | 9 ± 4* | 60 ± 30# |

TABLE 4-continued

Real-time PCR for quantification of relative expression levels of key metabolic enzymes and transport proteins under various experimental conditions.

|  | KO | KO + UDCA | KO + norUDCA |
|---|---|---|---|
| Mrp3 | 100 ± 33 | 194 ± 55 | 207 ± 73* |
| Mrp4 | 100 ± 30 | 357 ± 95 | 590 ± 193* |

NOTE.
Values are expressed as mean ± SD; n = 5 in each group, n.d., not detectable, KO, Mdr2 knock-out mice, KO + UDCA, UDCA-fed Mdr2 knock-out mice; KO + norUDCA, norUDCA-fed Mdr2 knock-out mice.
*$p < 0.05$, KO vs. KO + UDCA and KO vs. KO + norUDCA (ANOVA with Bonferroni post-testing)
$p < 0.05$, KO + UDCA vs. KO + norUDCA (ANOVA with Bonferroni post-testing)

Specific attention was paid to Sult2a1 and Mrp4, since sulfation and transport of sulfated compounds are inter-related to form a coordinately regulated pathway for excretion of sulfated steroids and bile acids (Schuetz, Strom, et al. 2001). norUDCA had no significant effects on mRNA expression of hepatocellular uptake (Ntcp, Oatp1) and canalicular efflux (Bsep, Mrp2) systems for bile acids and organic anions (data not shown). However, norUDCA resulted in a robust induction of phase I and II detoxification enzymes (Table 4) with most pronounced effects on Sult2a1 expression. In addition, norUDCA profoundly increased the expression of alternative basolateral efflux systems such as Mrp4 and—to a lesser degree—Mrp3 (Table 4, FIG. 7). The effects of UDCA were less pronounced (Table 4, FIG. 7). This coordinated induction of biotransformation pathways and efflux systems by norUDCA was accompanied by the appearance of bile acid glucuronides and also sulfates reflecting the functional implications of the observed expression changes.

1.3. Discussion

It could be shown that norUDCA cures sclerosing cholangitis in $Mdr2^{-/-}$ mice, a well characterized model system for PSC, within 4 weeks. In addition, it could be demonstrated that norUDCA is significantly more effective than UDCA.

The development of sclerosing cholangitis in $Mdr2^{-/-}$ is directly related to defective biliary phospholipid secretion and concomitantly increased biliary levels of non-micellar-bound toxic bile acids causing bile duct injury and pericholangitis (Fickert, Zollner, et al. 2002, Fickert, Fuchsbichler, et al. 2004). Induction of biliary bicarbonate secretion in norUDCA-fed $Mdr2^{-/-}$ presented by this example is strongly consistent with cholehepatic shunting of norUDCA (Hofmann 1977, Yoon, Hagey, et al. 1986). Increased biliary bicarbonate secretion (i) dilutes the toxic biliary content in $Mdr2^{-/-}$ and (ii) protects bile duct epithelial cells against oxidative stress since bicarbonate is a potent scavenger for reactive oxygen species. norUDCA stops therefore ongoing pericholangitis and subsequent periductal fibrosis in $Mdr2^{-/-}$ by minimizing bile duct epithelial cell injury from the bile duct lumen. This leads to the reconstitution of the cholangiocyte barrier function which would mean that the observed anti-inflammatory and anti-fibrotic effects of norUDCA in $Mdr2^{-/-}$ are secondary. However, it is evident that norUDCA has also direct anti-inflammatory and anti-fibrotic effects.

The findings of this example demonstrate that inhibition of periductal fibrosis, when accompanied with modulation of the biliary content (i.e. increasing the content of hydrophilic bile acids together with increased bicarbonate concentration within the duct), significantly improves liver injury in $Mdr2^{-/-}$.

In contrast to norUDCA, UDCA improved only periductal fibrosis of lobular bile ducts but increased serum ALT levels and induced bile infarcts in Mdr2$^{-/-}$. In a previous study with a shorter treatment period it was concluded that this may primarily be related to the choleretic effects of UDCA in the presence of unresolved biliary obstruction comparable to findings in CBDL UDCA-fed mice (Fickert, Zollner, et al. 2002). In contrast to this previous assumption, it was found only a trend for increased bile flow in UDCA- and even more so in norUDCA-fed Mdr2$^{-/-}$ in the current study using lower doses. However, since UDCA did not improve small duct disease in Mdr2$^{-/-}$ this does not exclude the possibility of increased biliary pressure at the level of the canals of Herring in UDCA-fed Mdr2$^{-/-}$ which could have led to the observed bile infarcts. The divergent effects of both bile acids in regard to liver injury are related to the differences in the level of bile secretion i.e. that norUDCA stimulates primarily ductular secretion whereas UDCA stimulates canalicular bile secretion upstream of the affected ducts.

A causal relationship between portal and lobular inflammation leading to periductal fibrosis and ductular proliferation as well as formation of hepatocellular carcinoma (HCC) in Mdr2$^{-/-}$ has recently been demonstrated (Fickert, Fuchsbichler, et al. 2004, Pikarsky, Porat, et al. 2004). In the current study norUDCA normalized hepatocyte and bile duct epithelial cell proliferation. Pikarsky et al. have demonstrated a reduction of inflammation and related HCC formation using the non-steroidal anti-inflammatory drug (NSAID) ibuprofen in this model (Pikarsky, Porat, et al. 2004). The therapeutic effects of NSAIDs and norUDCA may be combined and even amplified by sulindac, an NSAID, which undergoes cholehepatic shunting in rats (Bolder, Trang, et al. 1999).

Natural bile acids are efficiently N-acyl amidated (conjugated) in an amide linkage with glycine or taurine and then secreted into the bile canaliculus. In contrast, nor ($C_{23}$) bile acids have marked difference in their biotransformation and physiological properties when compared to their natural ($C_{24}$) homologues. It was shown that norUDCA results in a coordinated and robust induction of Sult2a1 (a transferase preferentially sulfating steroids and bile acids) and Mrp4 (a transporter of sulfated steroids and bile acids) (Schuetz, Strom, et al. 2001, Zelcer, Reid, et al. 2003). The functional implications of these findings are supported by the appearance of bile acid sulfates and glucuronides in urine of norUDCA fed Mdr2$^{-/-}$. Adaptive induction of bile acid detoxification by norUDCA via phase I (hydroxylation) and II (sulfation, glucuronidation) metabolism may result in better water soluble and therefore less toxic bile acid metabolites being eliminated by alternative hepatocellular efflux pumps (e.g. Mrp4) followed by their renal excretion as demonstrated in this example. The induction of such mechanisms by norUDCA was much more pronounced than that of UDCA (in this example) or agonistic ligands of CAR reported previously (Assem et al. 2004). This shows that norUDCA profoundly induces Sult2a1-mediated bile acid detoxification and export by adaptive overexpression of Mrp4 while norUDCA itself undergoes continued cholehepatic shunting. This has a dual beneficial effect by (i) displacing and diluting toxic bile acids in ductular bile and (ii) inducing a ductular bicarbonate-rich choleresis which reduces oxidative stress.

The generation of a bicarbonate rich choleresis by norUDCA has also therapeutic implications in human cholangiopathies (e.g. PSC, PBC, chronic liver graft rejection, non-suppurative destructive cholangitis), as cholehepatic shunting results in a continuing flux of molecules across the biliary ductular epithelium which helps altered bile ducts to better handle toxic/oxidative stress. For example, sulindac, a NSAID that also undergoes cholehepatic shunting in humans, has been shown to improve liver enzymes in PBC patients with incomplete response to UDCA treatment.

Of interest two parallels in the norUDCA metabolism between mice and humans exist which contrast previous observations in other rodents and experimental animals (e.g. biliary fistular rats, hamster, guinea pig). First both, mice and also men, show considerable renal excretion of norUDCA. In addition, it was also found that the major metabolite of norUDCA in mice was a glucuronide which is also in line with the findings in humans.

Second, in contrast to rats (Yoon, Hagey, et al. 1986) the estimated choleretic potency of norUDCA in mice and humans lays about three times above that of normal bile flow in both species. However, norUDCA induced bile flow to a much higher degree in rats (160 ml/min-kg). Nevertheless taken together these findings it could be shown that the effects of norUDCA in Mdr2$^{-/-}$ can be directly extrapolated to human cholestatic liver diseases.

In summary it could be shown that norUDCA cures sclerosing cholangitis in Mdr2$^{-/-}$. norUDCA is an effective compound for cholestatic liver diseases particularly for human PSC and liver diseases related to MDR3 mutations.

REFERENCES

Bolder et al. Gastroenterology 1999; 117(4):962-971.
Cohen et al. Gastroenterology 1986; 91(1):189-197.
Fickert et al. Gastroenterology 2001; 121(1):170-183.
Fickert et al. Gastroenterology 2002; 123(4):1238-1251.
Fickert et al. Gastroenterology 2004; 127(1):261-274.
Hofmann et al. Pediatr Transplant 1999; 3(3):219-224.
Jacquemin et al. Hepatology 1997; 25(3):519-523.
Jacquemin E. Clin Liver Dis 2000; 4(4):753-763.
Jansen et al. Liver Int 2003; 23(5):315-322.
Lammert et al. Hepatology 2004; 39(1):117-128.
Paumgartner et al. Hepatology 2002; 36(3):525-531.
Pikarsky et al. Nature 2004; 431(7007):461-466.
Schmassmann et al. Hepatology 1990; 11(6):989-996.
Trauner M et al. Aliment Pharmacol Ther 1999; 13(8):979-996.
Wagner et al. Gastroenterology 2003; 125(3):825-838.
Yoon et al. Gastroenterology 1986; 90(4):837-852.

The invention claimed is:

1. A method of treating an inflammatory cholestatic liver disease in a subject comprising:
   obtaining a pharmaceutical composition comprising nor-ursodeoxycholic acid and/or a pharmaceutically acceptable salt or ester thereof; and
   administering the pharmaceutical composition to the subject;
   wherein the inflammatory cholestatic liver disease is treated in the subject, and the inflammatory cholestatic liver disease is primary sclerosing cholangitis (PSC), primary biliary cirrhosis (PBC), progressive familial intrahepatic cholestasis, or drug-induced cholestasis.

2. The method of claim 1, wherein the inflammatory cholestatic liver disease is primary sclerosing cholangitis (PSC) or primary biliary cirrhosis (PBC).

3. The method of claim 2, wherein the inflammatory cholestatic liver disease is primary sclerosing cholangitis (PSC).

4. The method of claim 2, wherein the inflammatory cholestatic liver disease is primary biliary cirrhosis (PBC).

5. The method of claim 1, wherein the inflammatory cholestatic liver disease is drug-induced cholestasis.

* * * * *